United States Patent [19]

Meguro et al.

[11] Patent Number: 4,898,947
[45] Date of Patent: Feb. 6, 1990

[54] PYRIDINE AND THIAZOLIDINEDIONE DERIVATIVES

[75] Inventors: Kanji Meguro, Nishinomiya; Takeshi Fujita, Takarazuka; Chitoshi Hatanaka, Nagaokakyo; Satoru Ooi, Suita, all of Japan

[73] Assignee: Takeda Chemical Industries, Ltd., Osaka, Japan

[21] Appl. No.: 291,782

[22] Filed: Dec. 29, 1988

Related U.S. Application Data

[62] Division of Ser. No. 73,695, Jul. 19, 1987, Pat. No. 4,812,570.

[30] Foreign Application Priority Data

Jul. 24, 1986 [JP] Japan .................. 61-174278

[51] Int. Cl.$^4$ .................. C07D 213/46; C07D 413/12
[52] U.S. Cl. ..................................... 546/280; 546/340
[58] Field of Search .................. 546/280, 340

[56] References Cited

U.S. PATENT DOCUMENTS 4,725,610 2/1988 Meguro et al. .................. 514/369

FOREIGN PATENT DOCUMENTS 86100411 3/1985 China .................. 546/280

OTHER PUBLICATIONS

Sohda et al., Chem. Abstracts, vol. 98, No. 19; 160624h (1983).
March, J. Adv. Org. Chem., pp. 707–709.

*Primary Examiner*—Mary C. Lee
*Assistant Examiner*—J. Richter
*Attorney, Agent, or Firm*—Wenderoth, Lind & Ponack

[57] ABSTRACT

A compound of the formula:

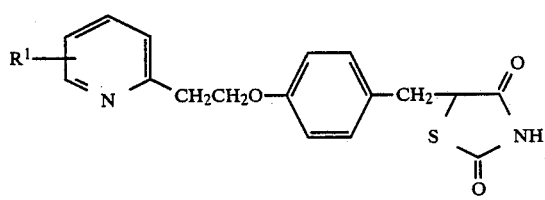

(wherein R$^1$ is hydrogen or a lower alkyl) can be produced advantageously by (1) reacting a compound of the formula:

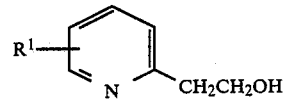

(wherein R$^1$ has the meaning given above) with a halogenating agent or sulfonyl halide to give a compound of the formula:

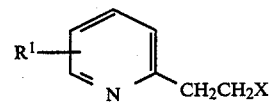

(wherein R$^1$ has the meaning given above and X is a halogen or an alkyl- or aryl-sulfonyloxy), (2) reacting the resulting compound with a compound of the formula:

to give a compound of the formula:

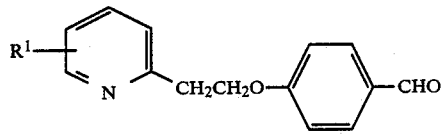

(wherein R$^1$ has the meaning given above), (3) reacting the resulting compound with a compound of the formula:

to give a compound of the formula:

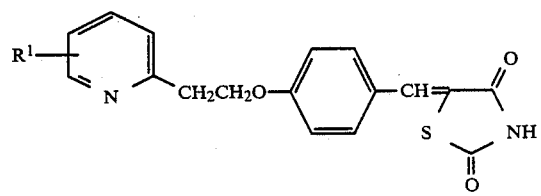

(wherein R$^1$ has the meaning given above), and (4) subjecting the resulting compound to catalytic reduction.

2 Claims, No Drawings

PYRIDINE AND THIAZOLIDINEDIONE DERIVATIVES

This application is a division of Ser. No. 07/073,695 filed July 14, 1987 now U.S. Pat. No. 4,812,570.

This invention relates to a novel method of producing thiazolidinedione derivatives having hypoglycemic and hypolipidemic activities.

Methods for production of various thiazolidinedione derivatives having hypoglycemic and hypolipidemic actions are described in Japanese Kokai Tokkyo Koho Sho 55-22636 and Sho 55-64586 and Chemical & Pharmaceutical Bulletin 30, 3563(1982), 30, 3580(1982), and 32, 2267(1984). These methods invariably comprise the steps of diazotizing an aniline derivative, condensing it with an acrylic ester in the presence of a copper catalyst by the so-called Meerwein arylation reaction to give a haloester, reacting it with thiourea to give an iminothiazolidine, and finally hydrolyzing the same. These methods include multi-step reaction processes. In particular, it is sometimes difficult to control the Meerwein reaction in an industrial production, since it is an exothermic reaction accompanied by generation of a large amount of nitrogen gas and thus could be dangerous. Moreover, because of the formation of by-products in the step of Meerwein arylation reaction, this route assures only insufficient yields and calls for a time-consuming purification procedure. Furthermore, special measures are required in the Meerwein reaction for elimination of an extremely bad odor of acrylic acid ester which must be used in excess and for disposal of the effluent containing a heavy metal. The above mentioned points make the known route disadvantageous both technically and commercially.

This invention provides a new commercially profitable method for the production of thiazolidinedione derivatives which have hypoglycemic and hypolipidemic activities and are of value as therapeutic agents for diabetes and hyperlipemia.

This invention relates to:

1. A method for producing a compound of the formula:

(I)

(wherein $R^1$ is hydrogen or a lower alkyl), which comprises reacting (1) a compound of the formula:

(II)

(wherein $R^1$ has the meaning given above) with a halogenating agent or a sulfonyl halide to give a compound of the formula (III)

(wherein $R^1$ has the meaning given above and X is a halogen or an alkyl- or aryl-sulfonyloxy) (2) reacting the resulting compound with a compound of the formula:

(IV)

to give a compound of the formula:

(V)

(wherein $R^1$ has the meaning given above), (3) reacting the resulting compound with a compound of the formula:

(VI)

to give a compound of the formula:

(VII)

(wherein $R^1$ has the meaning given above), and (4) subjecting the resulting compound to catalytic reduction.

2. A method for producing a compound of the formula (V) which comprises reacting a compound of the formula (II) with a halogenating agent or sulfonyl halide to give a compound of the formula (III) and then reacting the Compound (III) with a compound of the formula (IV).

3. A method for producing a compound of the formula (V) which comprises reacting a compound of the formula (II) with a compound of the formula:

(VIII)

to give a compound of the formula:

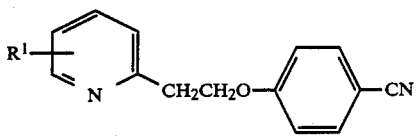

(wherein R¹ has the meaning given above), and then reacting the resulting compound with aqueous formic acid in the presence of Raney nickel alloy.

4. A method for producing a compound of the formula (I) which comprises reducing a compound of the formula (VII).

5. A compound of the formula (V).
6. A compound of the formula (VII).

Referring to the above general formulas (I), (II), (III), (V), (VII) and (IX), the lower alkyl group denoted by R¹ is a straight-chain or branched alkyl group of 1 to 6 carbon atoms, such as methyl, ethyl, propyl, isopropyl, butyl, isobutyl, sec-butyl, tert-butyl, pentyl, isopentyl, neopentyl, hexyl, etc. Among them, lower alkyl groups of 1 to 3 carbon atoms are preferable and ethyl is the most preferable. Such an alkyl group may be situated in any position of the pyridine ring. Halogen shown by X in the formula (III) includes chlorine, bromine and iodine; alkylsulfonyloxy shown by X includes methylsulfonyloxy, ethylsulfonyloxy and propylsulfonyloxy; and arylsulfonyloxy shown by X includes phenylsulfonyloxy and p-tolylsulfonyloxy. Particularly preferable ones are arylsulfonyloxy groups.

In the method of the present invention, first Compound (II) is reacted with a halogenating agent or sulfonyl halide to prepare Compound (III). As the halogenating agent, there may be mentioned thionyl chloride, phosphorus oxychloride, phosphorus tribromide, etc. As the sulfonyl halide, there may be mentioned such alkylsulfonyl halide having 1 to 4 carbon atoms as methylsulfonyl chloride, ethylsulfonyl chloride, propylsulfonyl bromide, such arylsulfonyl halide (phenyl or naphthyl which are unsubstituted or substituted by 1 to 3 alkyl groups of 1 to 4 carbon atoms) as phenylsulfonyl chloride, p-tolylsulfonyl chloride, p-tolylsulfonyl bromide. Among them, arylsulfonyl halide is preferable.

When halogenating agent is used, the reaction is carried out in a solvent such as dichloromethane, dichloroethane, chloroform, carbon tetrachloride, benzene, toluene, xylene, dimethylformamide, etc. The reaction temperature is in the range of −20° C. to 80° C., preferably −10° C. to 60° C.

When sulfonyl halide is used, the reaction is carried out in a solvent. The solvents include such halogenated aliphatic hydrocarbon as dichloromethane, dichloroethane, chloroform, carbon tetrachloride, such aromatic hydrocarbon as benzene, toluene, xylene, such ether as diethyl ether, dibutyl ether, diisobuthyl ether, ethyleneglycol diethyl ether, dioxane, tetrahydrofuran, water, ethyl acetate, dimethylformamide or a mixture of two or more of these solvents. The reaction is usually carried out in the presence of an inorganic base (e.g. sodium hydroxide, potassium hydroxide, potassium carbonate, sodium carbonate, etc.) or an organic base (e.g. triethylamine, morpholine, N-ethylpiperidine, etc.). Further the reaction is advantageously carried out in the presence of a phase transfer catalyst such as benzyl tributylammonium bromide, benzyl triethylammonium chloride, tetrabutylammonium bromide, cetyl trimethylammonium chloride. The sulfonyl halide is used in an amount of 1 to 2 moles, preferably 1.0 to 1.5 moles per mole of Compound (II). The base is used in an amount of 1 to 3 moles, preferably 1.5 to 2.5 moles per mole of Compound (II). The phase transfer catalyst is used in an amount of 0.1 to 1.0 mole, preferably 0.2 to 0.5 mole per mole of Compound (II). The reaction temperature is usually 0° C. to 50° C., preferably 15° C. to 30° C.

The reaction time is usually not less than 2 hours, preferably 3 to 5 hours though it varies with a reaction condition such as reaction temperature.

The reaction between Compound (III) and Compound (IV) is usually carried out in the presence of a base in a suitable solvent. Further, the reaction advantageously proceeds in the presence of a phase transfer catalyst. As the solvent, the base and the phase transfer catalyst, those used in the reaction between Compound (II) and the sulfonyl halide can be used. Compound (IV) is used in an amount of 1 to 3 moles, preferably 1 to 1.5 mole, per moles of Compound (III). The base is used in an amount of 1 to 3 moles, preferably 1.5 to 2.5 moles, per mole of Compound (III). When a phase transfer catalyst is used in the reaction, the amount of the catalyst is usually 0.1 to 1.0 mole, preferably 0.2 to 0.5 mole, per mole of Compound (III). The reaction temperature is usually 20° C. to 90° C., preferably 50° C. to 65° C. The reaction time is usually not less than 5 hours, preferably 10 to 20 hours. It is advantageous, from the industrial point of view, to use a sulfonyl halide in the reaction to convert Compound (II) to Compound (III) since the reaction mixture containing Compound (III) can be used, without isolating the Compound (III), for the next reaction to give Compound (V).

Compound (II) can also be converted to Compound (V), for example, by the following processes.

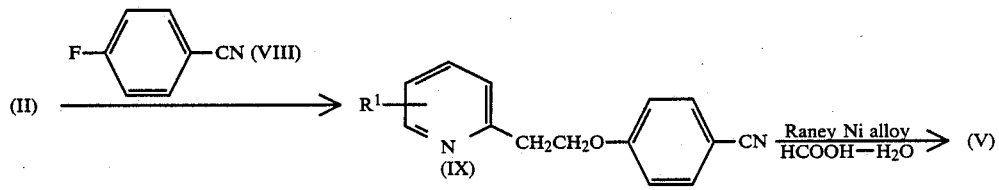

[wherein R¹ has the meaning defined hereinbefore]

The conversion of Compound (II) to Compound (IX) is effected by condensing (II) with (VIII) in the presence of, for example, sodium hydride. This reaction can be conducted in a solvent such as dimethylformamide, dimethyl sulfoxide, tetrahydrofuran, dimethoxyethane, etc. at −10° C. to 30°0 C. The subsequent conversion of Compound (IX) to Compound (V) is effected by heating (IX) together with Raney nickel alloy in aqueous formic acid. The reaction between Compound (V) and Compound (VI) is usually carried out in a suitable solvent in the presence of an appropriate base. As such solvent-base system, there may be employed a suitable combination of a solvent such as alcohols (for example, methanol, ethanol, propanol, 2-propanol, butanol, isobutyl alcohol, 2-methoxyethanol, etc.), dimethylformamide, dimethyl sulfoxide, sulfolane, acetonitrile, dioxane, dimethoxyethane, acetic acid, etc. with a base such as amines (for example, ammonia, methylamine, ethylamine, n-butylamine, pyrrolidine, piperidine, morpholine, piperazine, diethylamine, diisoproylamine, triethylamine, etc.), sodium alkoxides (for example, sodium methoxide, sodium ethoxide, etc.), potassium carbonate, sodium carbonate, sodium hydroxide, sodium acetate, potassium acetate, and so on. Compound (VI) is generally used in a proportion of 1 to 4 moles and preferably 1 to 2.5 moles per mole of Compound (V). The base is generally used in a proportion of 0.05 to 1.0 mole and preferably 0.3 to 0.5 mole per mole of Compound (V). This condensation reaction is conducted generally at 40° C. to reflux temperature and preferably at 60° C. to reflux temperature. The reaction time is generally 0.5 to 50 hours.

Then, Compound (VII) is reduced to produce Compound (I). In this step, Compound (VII) is subjected to catalytic reduction in a suitable solvent in the presence of a catalyst. As the solvent, there may be employed, among others, alkanols such as methanol, ethanol, propanol, etc., ethers such as dioxane, dimethoxyethane, tetrahydrofuran, etc., ethyl acetate, acetic acid, dimethylformamide, N-methylpyrrolidone, etc., either alone or in combination. As the catalyst, there can be employed palladium black, palladium on carbon, palladium on barium sulfate, palladium on barium carbonate, platinum oxide, platinum on carbon and so on. The reaction temperature is usually 0° C. to 180° C., preferably 50° C. to 120° C. Though the reaction proceeds under atmospheric pressure, it may be conducted under a pressure of not more than 150 kg/cm$^2$, preferably 30 kg/cm$^2$ to 100 kg/cm$^2$.

The resulting thiazolidinedione derivative (I) can be easily separated and purified by known isolation and purification procedures. Particularly, the Compound (I) can be isolated in high quality either by recrystalizing from dioxane, acetic acid-acetone, acetic acid-water or acetic acid-ethanol or by dissolving Compound (I) in hydrochloric acid, aqueous sulfuric acid or aqueous methane sulfonic acid followed by neutralizing the solution with sodium hydrogencarbonate, ammonia, etc. to crystalize Compound (I).

Further, as (I) forms salts with bases, it can be isolated in the form of a salt. As examples of such salt, there can be mentioned the sodium salt, potassium salt, magnesium salt, ammonium salt, triethylammonium salt, piperidinium salt, morpholinium salt, phenylethylammonium salt, and so on.

The Compound (I) produced by the method of this invention or a pharmacologically acceptable salt thereof exhibits blood-glucose and blood-lipid lowering action with lower toxicity, and may be safely administered, orally or parenterally, as it is or advantageously as a pharmaceutical composition comprising an effective amount of the compound (I) or its pharmacologically acceptable salt and a pharmaceutically acceptable carrier, excipient or diluent therefor, in the form of, for example, powder, granule, tablet, hard capsule, soft capsule, dry syrup, suppository, injection or the like.

The composition for oral administration such as powder, granule, tablet, hard capsule, soft capsule and dry syrup may be prepared by a per se known conventional manner, and may comprise carriers, excipients or diluents conventionally used in the pharmaceutical art. For example, suitable carriers or excipients include lactose, starch, sugar, magnesium stearate, etc. As the excipients in the preparation of soft capsules, there my be used nontoxic, pharmaceutically acceptable oils and fats of animal, vegetable or mineral origin. The essential active ingredients are generally dissolved in these oils and fats before filling soft capsules therewith.

The compositions for parenteral administration may, for example, be injections, and suppositories. The injectable preparations may be prepared in the form of solutions or suspensions. Injectable preparations in the form of aqueous solutions may be prepared by a conventional manner. The suppositories for rectal administration can be prepared by incorporating the compound (I) or its pharmacologically acceptable salt with a conventional suppository base. The pharmaceutical composition of the present application can be used as an antidiabetic agent for mammals including man.

Oral administration to an adult patient is 0.05–10 mg/kg body weight/day, preferably 0.5–5 mg/kg body weight/day, and parenterally 0.01–10 mg/kg body weight/day, preferably 0.01–1.0 mg/kg body weight/day once daily or divided into 2–4 times a week.

The method of the present invention involves only four steps to produce the desired Compound (I) from Compound (II) which is commercially available. Further in the present method, it is unnecessary to use either acrylic acid ester which has a bad smell, or a heavy metal which should not be dumped together with waste fluid from the viewpoint of environmental pollution. The present methiod can avoid the Meerwein reaction which is difficult to conduct on an industrial scale. Thus the present method is advantageous from the industrial point of view.

EXAMPLE 1

[Production of Compound (V) from Compound (II) via Compound (III)]

(a) To a solution of sodium hydroxide (5 g) in water (30 ml), were added methylene chloride (100 ml), 5-ethyl-2-pyridineethanol (15 g) and benzyltributylammonium chloride (50% aqueous solution, 6 g), p-toluenesulfonyl chloride (23 g), and the mixture was stirred at room temperature for 2 hours. To the reaction mixture were added p-hydroxybenzaldehyde (12 g), water (100 ml) and sodium hydroxide (8 g) and the mixture was stirred at 40°–50° C. for 12 hours. The reaction mixture was separated into two phases and the methylene chloride layer was dried (MgSO$_4$) and concentrated to give 28.6 g of crude 4-[2-(5-ethyl-2-pyridyl)ethoxy]benzaldehyde as oil. This oil was purified by silica gel chromatography to give 15.8 g (62%) of pure 4-[2-(5-ethyl-2-pyridyl)ethoxy]benzaldehyde as oil.

NMR(CDCl$_3$) δ: 1.15 (t, 3H), 2.6 (q, 2H), 3.2 (t, 2H), 4.4 (t, 2H), 6.89–8.35 (m, 7H), 9.88 (s, 1H).

(b) To a mixed solution of 5-ethyl-2-pyridine ethanol (6.0 kg), benzyltributylammonium chloride (6.2 kg of 50% aqueous solution), 1,2-dichloroethane (30 l) and p-toluenesulfonylchloride (9.2 kg) was added dropwise 8N aqueous solution (10 l) of sodium hydroxide at 25° C. After the solution was stirred at 22±3° C. for 4 hours, p-hydroxybenzaldehyde (5.9 kg) and 3N solution (16 l) of sodium hydroxide, were added, and the mixed solution was stirred at 57±3° C. for 15 hours. After the solution was cooled, water (70 l) was added. The aqueous layer was separated and subjected to extraction with 1,2-dichloroethane (20 l). The organic layers were combined and the combined layer was washed three times with 0.1N aqueous solution of sodium hydroxide and three times with water (30 l). The organic layer was concentrated at not higher than 45° C. under a reduced pressure, whereby 4-[2-(5-ethyl-2-pyridyl)ethoxy]benzaldehyde was obtained as an oil. Quantitative analysis by HPLC (high performance liquid chromatography) showed that 5.98 kg (59.0%) of 4-[2-(5-ethyl-2-pyridyl)ethoxy]benzladehyde was included in this crude product.

(c) By a similar manner to Example (1-a), the reaction was carried out by using benzyltriethylammonium chloride as a phase transfer catalyst, whereby 8.3 g (32.5%) of 4-[2-(5-ethyl-2-pyridyl)ethoxy]benzaldehyde was obtained as an oil.

(d) In a similar manner to Example (1-b), the reaction was carried out by using carbontetrachloride as a solvent and 30 g of 5-ethyl-2-pyridinethanol. Quantitative analysis by HPLC showed that 55.3% of 4-[2-(5-ethyl-2-pyridyl)ethoxy]benzaldehyde was included in the crude product obtained in the above.

EXAMPLE 2

[Production of Compound (VII) from Compound (V)]

(a) A mixture of 4-[2-(6-methyl-2-pyridyl)ethoxy]benzaldehyde (1.21 g), 2,4-thiazolidinedione (0.59 g), ethanol (50 ml) and piperidine (0.33 g) was heated under reflux for 16 hours. The reaction mixture was poured into ice-water and acidified with acetic acid. The resulting crystals were collected by filtration to give 5-{4-[2-(6-methyl-2-pyridyl)ethoxy]benzylidene}-2,4-thiazolidinedione. Yield: 1.34 g (78.5%). Recrystallization from methanol gave pale yellow prisms. m.p.: 180.5°–182° C.

Elemental analysis, for $C_{18}H_{16}N_2O_3S$ Calcd.: C, 63.51; H, 4.74; N, 8.23. Found: C, 63.40; H, 4.84; N, 8.30.

(b) A mixture of 4-[2-(5-ethyl-2-pyridyl)ethoxy]benzaldehyde (2.40 g), 2,4-thiazolidinedione (1.66 g), ethanol (40 ml) and piperidine (0.2 ml) was heated under reflux for 8 hours. The resulting crystals were recrystallized form ethyl acetate to give 2.14 g (64%) of 5-{[2-(5-ethyl-2-pyridyl)ethoxy]benzylidene}-2,4-thiazolidinedione as colorles crystals. m.p.: 165.5°–167° C.

Elemental analysis, for $C_{19}H_{18}N_2O_3S$ Calcd.: C, 64.39; H, 5.12; N, 7.90. Found: C, 64.29; H, 5.19; N, 7.64.

(c) A mixture of 4-[2-(5-ethyl-2-pyridyl)ethoxy]benzaldehyde (5.56 kg), 2,4-thiazolidinedione (6.7 kg), piperidine (1.4 l) and ethanol (80 l) was refluxed for 5 hours. The reaction mixture was gradually cooled and resulting crystals were collected by filtration. The crystals were washed with ethanol (20 g), dried, and subjected to recrystallization from 1,2-dichloroethane (120 l). The resulting crystals were collected by filtration. The crystals were washed with 1,2-dichloroethane (15 l) and dried under reduced pressure whereby 4.87 kg (63.1%) of crystals of 5-{4-[2-(5-ethyl-2-pyridyl)ethoxy]benzylidene}-2,4-thiazolidinedione were obtained.

(d) A mixture of 4-[2-(5-ethyl-2-pyridyl)ethoxy]benzaldehyde (27 g), ethanol (300 ml), 2,4-thiazolidinedione (33 g) and concentrated aqueous ammonia (14 ml) was heated under reflux for 5 hours. The precipitated crystals were separated. Recrystallization from 1,2-dichloroethane gave 21.6 g (57.6%) of crystals of 5-{4-[2-(5-ethyl-2-pyridyl)ethoxy]benzylidene}-2,4-thiazolidinedione.

EXAMPLE 3

[Production of Compound (I) from Compound (VII)]

(a) To a solution of 5-{4-[2-(6-methyl-2-pyridyl)ethoxy]benzylidene}-2,4-thiazolidinedione (400 mg) in dioxane (60 ml) was added 5% palladium on carbon (1.2 g) and catalytic reduction was carried out at atmospheric pressure for 6 hours. The catalyst was filtered off and the filtrate was concentrated. The residue was recrystallized from 70% ethanol to give 5-{4-[2-(6-methyl-2-pyridyl)ethoxy]benzyl}-2,4-thiazolidinedione as crystals. Yield: 218 mg (54.2%); m.p.: 156°–157° C.

Elemental analysis, for $C_{18}H_{18}N_2O_3S$ Calcd.: C, 63.14; H, 5.30; N, 8.18. Found: C, 63.03; H, 5.19; N, 8.41.

(b) To a dimethylformamide solution of 5-{4-[2-(5-ethyl-2-pyridyl)ethoxy]benzylidene}-2,4-thiazolidinedione (1.0 g) was added palladium black (0.2 g) and catalytic reduction was carried out at 50° C. and 50 kg/cm² for 5 hours. The catalyst was filtered off and the filtrate was concentrated to dryness. The residue was dissolved in 6N-hydrochloric acid and the solution was neutralized with sodium hydrogen carbonate to give 5-{4-[2-(5-ethyl-2-pyridyl)ethoxy]benzyl}-2,4-thiazolidinedione as crystals. Yield: 650 mg (64.8%); m.p.: 173°–174° C.

Elemental analysis, for $C_{19}H_{20}N_2O_3S$ Calcd.: C, 64.02; H, 5.66; N, 7.86. Found: C, 63.73; H, 5.65; N, 7.84.

(c) To a solution of 5-{4-[2-(5-ethyl-2-pyridyl)ethoxy]benzylidene}-2,4-thiazolidinedione (600 g) in dimethylformamide (1.2 l) was added palladium on carbon (600 g). The mixture was heated at 50° C. to 55° C. under 50 kg/cm² for 2 hours. The catalyst was filtered off and water was added to the filtrate. The resulting crystals were collected by filtration and washed with water. Recrystallization from dioxane (8.5 l) gave crystals of 5-{4-[2-(5-ethyl-2-pyridyl)ethoxy]benzyl}-2,4-thiazolidinedione. Yield: 380.9 g (63.1%).

(d) 5-{4-[2-(5-Ethyl-2-pyridyl)ethoxy]benzylidene}-2,4-thiazolidinedione (10 g) was dissolved in acetic acid (200 ml). To the solution was added 5% palladium on carbon (50% wet, 20 g). The mixture was hydrogenated at 55° C. to 60° C. under 40 to 50 kg/cm² for 2 hours. After removing the catalyst by filtration, the filtrate was concentrated to about 80 ml. To the concentrate was added acetone (800 ml). The resulting crystals of 5-{4-[2-(5-ethyl-2-pyridyl)ethoxy]benzyl}-2,4-thiazolidinedione was collected by filtration. Yield: 6.81 g (67.7%).

(e) To a solution of 5-{4-[2-(5-ethyl-2-pyridyl)ethoxy]benzylidene}-2,4-thiazolidinedione (10 g) in dioxane (200 ml) was added 5% palladium on carbon (5 g). The mixture was heated at 100° C. under 50 kg/cm² for 2 hours. The catalyst was filtered off, and the filtrate was concentrated to about 70 ml under reduced pressure. The resulting crystals were collected by filtration and dried at 50° C. under a reduced pressure to give 7.2 g of crude crystals. Recrystallization from acetic acid-water gave crystals of 5-{4-[2-(5-ethyl-2-pyridyl)ethoxy]benzyl}-2,4-thiazolidinedione. Yield: 6.42 g (63.8%).

(f) The crude product of 5-{4-[2-(5-ethyl-2-pyridyl)ethoxy]benzyl}-2,4-thiazolidinedione obtained by a similar manner to Example (3-e) was subjected to recrystallization by using acetic acid-ethanol as a recrystallization solvent to yield a pure sample. Yield: 5.85 g (58.2%).

REFERENCE EXAMPLE 1

[Production of Compound (IX) from Compound (II)]

To a mixture of 6-methyl-2-pyridineethanol (97.2 g), p-fluorobenzonitrile (85.8 g) and dry tetrahydrofuran (600 ml) was added 60% sodium hydride in oil (29.0 g) in small portions with ice-cooling and stirring and the mixture was further stirred for 2 hours. The reaction mixture was poured in ice-water and extracted with ethyl ether. The ethyl ether layer was washed with water, dried (MgSO$_4$) and concentrated, and the residue was crystallized from hexane to give 4-[2-(6-methyl-2-pyridyl)ethoxy]benzonitrile. Yield: 85.9 g (50.1%); m.p.: 66°–67° C.

REFERENCE EXAMPLE 2

[Production of Compound (V) from Compound (IX)]

A mixture of 4-[2-(6-methyl-2-pyridyl)ethoxy]benzonitrile (9.62 g), Raney nickel alloy (10.0 g) and 75% formic acid (150 ml) was heated under reflux for 1 hour. The reaction mixture was filtered and the filtrate was concentrated. The residue was diluted with water, alkalinized with 4N-KOH, and extracted with ethyl ether. The ethyl ether layer was washed with water and dried (MgSO$_4$) and the solvent was distilled off. The residue was recrystallized from ethyl etherhexane to give 4-[2-(6-methyl-2-pyridyl)ethoxy]benzaldehyde.

Yield: 6.20 g (63.6%); m.p.: 53°–55° C.

We claim:

1. A compound of the formula:

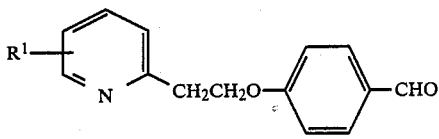

wherein R$^1$ is hydrogen or a lower alkyl.

2. A compound of the formula:

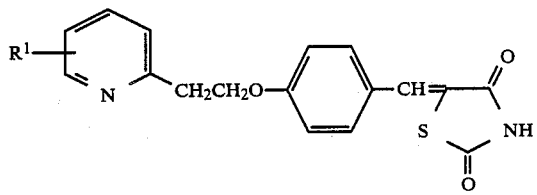

wherein R$^1$ is hydrogen or a lower alkyl.

* * * * *